(12) United States Patent
Shaykova

(10) Patent No.: US 10,264,875 B2
(45) Date of Patent: Apr. 23, 2019

(54) DENTAL FINGER GLOVES

(71) Applicant: Aleksandra Shaykova, Altamonte Springs, FL (US)

(72) Inventor: Aleksandra Shaykova, Altamonte Springs, FL (US)

(*) Notice: Subject to any disclaimer, the term of this patent is extended or adjusted under 35 U.S.C. 154(b) by 0 days.

(21) Appl. No.: 14/618,856

(22) Filed: Feb. 10, 2015

(65) Prior Publication Data

US 2016/0227978 A1 Aug. 11, 2016

(51) Int. Cl.
*A61C 15/00* (2006.01)
*A46B 5/04* (2006.01)
*A61C 15/04* (2006.01)
*A46B 9/00* (2006.01)

(52) U.S. Cl.
CPC .............. *A46B 5/04* (2013.01); *A46B 9/005* (2013.01); *A61C 15/046* (2013.01)

(58) Field of Classification Search
CPC ...... A61C 15/00; A41D 19/00; A41D 19/001; A41D 19/0041; A41D 13/087; A46B 5/04; A61B 42/10; A63B 31/02
See application file for complete search history.

(56) References Cited

U.S. PATENT DOCUMENTS

| | | | | |
|---|---|---|---|---|
| 1,896,941 A | * | 2/1933 | Cohen | A46B 5/04 15/227 |
| 3,675,264 A | * | 7/1972 | Storandt | A46B 5/04 15/104.94 |
| 3,902,509 A | * | 9/1975 | Tundermann | A61C 15/02 15/104.93 |
| 4,665,901 A | | 5/1987 | Spector | |
| 4,884,581 A | * | 12/1989 | Rescigno | A61B 13/00 128/869 |
| 4,992,705 A | * | 2/1991 | Hathaway, II | H05B 41/40 315/210 |
| D323,722 S | * | 2/1992 | Lott | D28/68 |
| 5,213,428 A | * | 5/1993 | Salman | A46B 5/04 15/167.1 |
| 5,280,661 A | * | 1/1994 | Brown | A47L 13/18 15/214 |
| 5,320,531 A | * | 6/1994 | Delizo-Madamba | A61C 19/00 15/227 |

(Continued)

FOREIGN PATENT DOCUMENTS

DE 3232313 A1 3/1984
EP 1 900 302 A1 3/2008
(Continued)

OTHER PUBLICATIONS

International Search Report and Written Opinion dated May 26, 2016 in connection with Application No. PCT/US2016/016716.

*Primary Examiner* — Rachel R Steitz
(74) *Attorney, Agent, or Firm* — Wolf, Greenfield & Sacks, P.C.

(57) ABSTRACT

In at least one aspect of this disclosure, a dental finger glove device can include a first finger portion configured to fit on a first digit of a user and a second finger portion configured to fit on a second digit of a user and connected to the first finger portion. An outer surface of the finger portion can include a mesh material for massaging teeth. The mesh material can include gauze or any other suitable material.

17 Claims, 4 Drawing Sheets

(56) References Cited

U.S. PATENT DOCUMENTS

| | | | | |
|---|---|---|---|---|
| 5,348,153 A * | 9/1994 | Cole | ................ | A46B 5/04 15/167.1 |
| 5,765,252 A * | 6/1998 | Carr | ................ | A46B 5/04 15/104.94 |
| 6,009,557 A * | 1/2000 | Witta | ................ | A41D 13/087 2/159 |
| 6,019,773 A * | 2/2000 | Denmark | ................ | A46B 5/04 606/161 |
| 6,647,549 B2 | 11/2003 | McDevitt et al. | | |
| 6,687,911 B2 * | 2/2004 | Fitz | ................ | A41D 19/0075 2/163 |
| 7,020,898 B1 * | 4/2006 | Pucci | ................ | A01K 13/001 2/161.6 |
| 7,127,771 B2 * | 10/2006 | McDevitt | ................ | 132/323 |
| D533,314 S * | 12/2006 | Schiazza | ................ | D29/113 |
| 7,380,289 B2 * | 6/2008 | Kordecki, Jr. | ..... | A41D 19/0055 2/161.6 |
| 8,539,614 B2 * | 9/2013 | Cote | ................ | A41D 13/087 2/161.1 |
| 8,887,314 B2 * | 11/2014 | Bormann-Early | ... | A41D 13/087 2/161.8 |
| 8,943,612 B2 * | 2/2015 | Jeong | ................ | A41D 19/0055 2/161.8 |
| 2003/0056274 A1 * | 3/2003 | Sorrels | ................ | A61B 19/04 2/21 |
| 2003/0226574 A1 * | 12/2003 | Padar | ................ | A61C 15/043 132/325 |
| 2006/0225764 A1 * | 10/2006 | Mark | ................ | A61C 15/043 132/321 |
| 2008/0227055 A1 | 9/2008 | Seidman | | |
| 2012/0016416 A1 | 1/2012 | Frazier | | |

FOREIGN PATENT DOCUMENTS

| | | | |
|---|---|---|---|
| EP | 1 267 663 B1 | 7/2011 | |
| GB | 2352975 A * | 2/2001 | ............... A46B 5/04 |
| GB | 2442063 A * | 3/2008 | ............... A46B 5/04 |

\* cited by examiner

DENTAL FINGER GLOVES

BACKGROUND

1. Field

The present disclosure relates to dental devices, more specifically to finger gloves for dental care.

2. Description of Related Art

Dental cleaning wipes, in certain cases, have included a finger sleeve for fitting a single finger on a user's hand. Certain devices implement a mesh attached to the finger sleeve or forming the finger sleeve. Traditional finger gloves do not allow for brushing of both sides of teeth simultaneously and/or lack controllability. Additionally, these devices lead to the user's hands becoming soaked with water, saliva, dentifrice, or the other liquids. Consequently, traditional devices are not suitable as a substitute for a toothbrush.

Such conventional devices, methods, and systems have generally been considered satisfactory for their intended purpose. However, there is still a need in the art for improved dental devices. The present disclosure provides a solution for this need.

SUMMARY

In at least one aspect of this disclosure, a dental finger glove device can include a first finger portion configured to fit on a first digit of a user and a second finger portion configured to fit on a second digit of a user and connected to the first finger portion. An outer surface of the finger portion can include a mesh material for massaging teeth. The mesh material can include gauze or any other suitable material.

The first digit can be a thumb and the second digit can be an index finger. In certain embodiments, the first finger portion and the second finger portion can be connected together at a base of each portion with dental floss.

In certain embodiments, the device can further include an elastic two-finger glove underneath the mesh material defining the first finger portion and the second finger portion. The elastic two-finger glove can include at least one of rubber, latex, and/or other non-latex elastic.

Dental floss can be connected to an inner surface of the elastic two-finger glove. In certain embodiments, the dental floss can be perforated at a connection point to the elastic two-finger glove such that it can be removed therefrom.

The mesh can be impregnated with a dental compound. The dental compound can include at least one of toothpaste, mouthwash, hydrogen peroxide, baking soda, Xylitol, Calcium Phosphate, Recaldent, Fluoride, Chlorhexidine, Propolis, an antioxidant, a neutralizing pH compound, an alkalizing pH compound, a foaming compound, a mechanical debridement compound, a chemical debridement compound, a biological debridement compound, vitamin E, vitamin A, vitamin C, vitamin K, Aloe Vera, chamomile or components thereof, mint or components thereof, peppermint or components thereof, cucumber extract or components thereof, carrot extract or components thereof.

In certain embodiments, the mesh material can be wetted and packaged such that a user need not wet the device before use. A securement member can be attached to and extend from at least one of the first finger portion and the second finger portion for securing the device to a user's hand. The securement member can be an elastic band for securing to the wrist of a user.

In accordance with at least one aspect of this disclosure, a method for manufacturing a dental device includes forming an elastic two-finger glove and disposing a mesh material on an outer surface of the elastic two finger glove. The method can further include coupling a dental floss to an inner surface of the elastic two-finger glove.

Coupling the dental floss to an inner surface of the elastic two-finger glove includes removably coupling the dental floss to the inner surface of the elastic two-finger glove. Removably coupling the dental floss to an inner surface of the elastic two-finger glove includes perforating a connection point of the dental floss.

The method can further include disposing a dental compound on or within the mesh material. In certain embodiments, the method can further include wetting the mesh material and packaging the dental device in a wetted state.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1A:
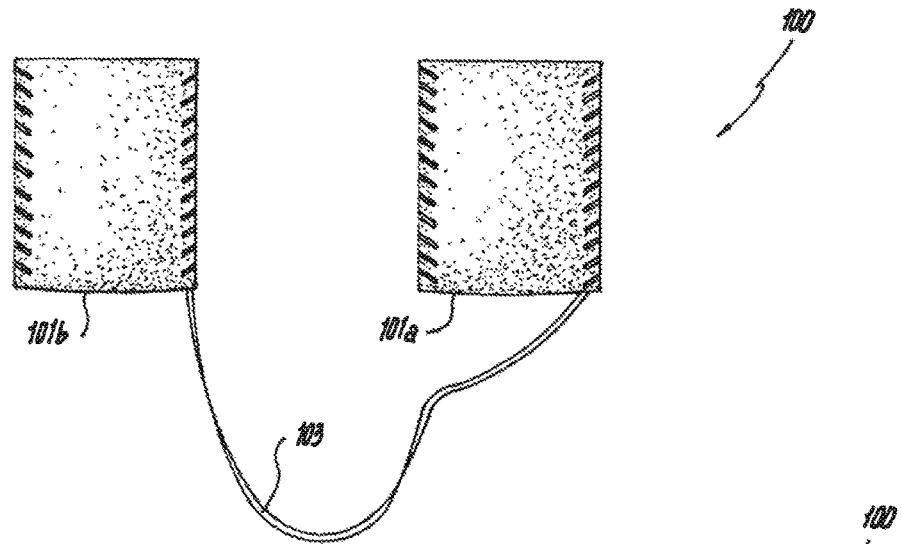
FIG. 1A is a perspective view of an embodiment of a dental finger glove device in accordance with this disclosure.

Reference will now be made to the drawings wherein like reference numerals identify similar structural features or aspects of the subject disclosure. For purposes of explanation and illustration, and not limitation, an illustrative view of an embodiment of a dental finger glove device in accordance with the disclosure is shown in FIG. 1 and is designated generally by reference character 100. Other embodiments and/or other aspects of this disclosure are shown in FIGS. 2A-3C. The devices and methods described herein can be used for dental care and prophylaxis.

Figure 1B:
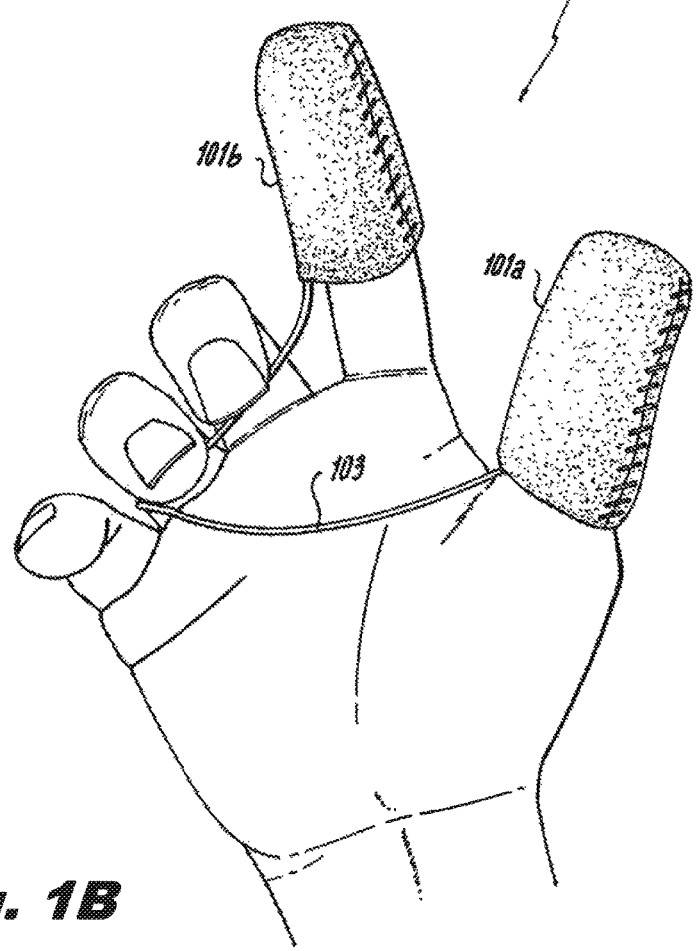
FIG. 1B is a perspective view of the device of FIG. 1A, shown disposed on a hand.

Referring to FIGS. 1A and 1B, an embodiment of a dental finger glove device 100 can include a first finger portion 101a configured to fit on a first digit of a user and a second finger portion 101b configured to fit on a second digit of a user. Each finger portion 101a, 101b can be made of a mesh material for massaging teeth. For example, the mesh material can include gauze (e.g., woven, non-woven as shown), non-woven sponge, or any other suitable material.

The mesh material can be configured to create foaming effect for toothpaste and/or to debride the gums and teeth. The texture of the mesh material can increase the tactile sensitivity while the user is rubbing the mesh material against gums and teeth, enhance the cleansing capabilities for removing plaque (biofilm over the teeth), and/or enhance the retention and foaminess of a dentifrice used therewith. While the finger portions 101a, 101b are shown as being only made of the mesh material, it is contemplated that one or more of the finger portions 101a, 101b can include a liquid sealing barrier (e.g., an elastic layer) on an inner surface of each finger portion 101a, 101b to prevent liquid from soaking through to the users hand.

The mesh can be impregnated with a dental compound. The dental compound can include at least one of toothpaste, mouthwash, hydrogen peroxide, baking soda, Xylitol, Calcium Phosphate, Recaldent, Fluoride, Chlorhexidine, Propolis, an antioxidant, a neutralizing pH compound, an alkalizing pH compound, a foaming compound, a mechanical debridement compound, a chemical debridement compound, a biological debridement compound, vitamin E, vitamin A, vitamin C, vitamin K, Aloe Vera, chamomile or components thereof, mint or components thereof, peppermint or components thereof, cucumber extract or components thereof, carrot extract or components thereof. Any other suitable compositions for dental care, general healthcare, or other compounds are contemplated herein.

The mesh material can include a single layer, double layer, or any other suitable number of layers and/or wraps. It is contemplated that embodiments having a multilayer design can enhance retention of a dentifrice, increase foaming action, and/or increase strength against tearing and/or disintegrating. It is also contemplated that the mesh material can include any suitable bristles (e.g., mini-bristles) disposed thereon for brushing action.

As shown, the first finger portion 101a can be connected to the second finger portion 101b at a base portion thereof with dental floss 103. The dental floss 103 can be removably connected in any suitable manner (e.g., tying, perforating part of the dental floss 103 to be torn) to the finger portions 101a, 101b such that a user can tear or otherwise remove at least one end of the dental floss 103 from the finger portions 101a, 101b. It is also contemplated that the dental floss 103 can be permanently affixed at its ends to one or both of the finger portions 101a, 101b via any suitable means (e.g., stitching, adhering) such that it is not intended to be removed from the finger portions 103a, 103b.

In certain embodiments, the first finger portion 101a can be configured to fit a thumb and the second finger portion 101b can be configured to fit an index finger. As shown, the dental finger glove device 100 can be used on either a right hand or a left hand of a user because the mesh covers both sides. However, it is contemplated that only one side of device 100 can be configured for dental care, thus limiting use of the device 100 to one hand (i.e., left or right). For example, the mesh material may be disposed only on one side and/or at distal portions of the finger portions 101a, 101b.

In certain embodiments, a dental finger glove device 200 can include an elastic two-finger glove 207 underneath a mesh material layer 205. The mesh material layer 205 can be made from any suitable mesh material as described above and can be impregnated with any suitable dental compound as described above. The elastic two-finger glove 207 defines the first finger portion 201a and the second finger portion 201b for a user to insert their fingers into (e.g., a thumb and index finger as shown).

The elastic two-finger glove 207 can be made from at least one of rubber, latex, non-latex, or any other suitable elastic material. For example, the elastic two-finger glove 207 can include any suitable material (e.g., Teflon tape, nitrile butadiene rubber, powder free Nytrile, Latex). This can allow fir sterile use due to liquid and/or bodily fluid isolation from the users hand and the teeth/gums of the user or someone else (e.g., for medical or dental patients). The elastic two-finger glove 207 can be configured to fit any suitable hand size or age range (e.g., kids, adults).

In certain embodiments, the first finger portion 201a can be configured to fit a thumb and the second finger portion 201b can be configured to fit an index finger. As shown, the dental finger glove device 200 can be used on either a right hand or a left hand of a user. However, it is contemplated that only one side of device 200 can be configured for dental care, thus limiting use of the device 200 to one hand (i.e., left or right). For example, the mesh material layer 205 may be disposed only on one side and/or at distal portions of the finger portions 201a, 201b.

Figure 2A:
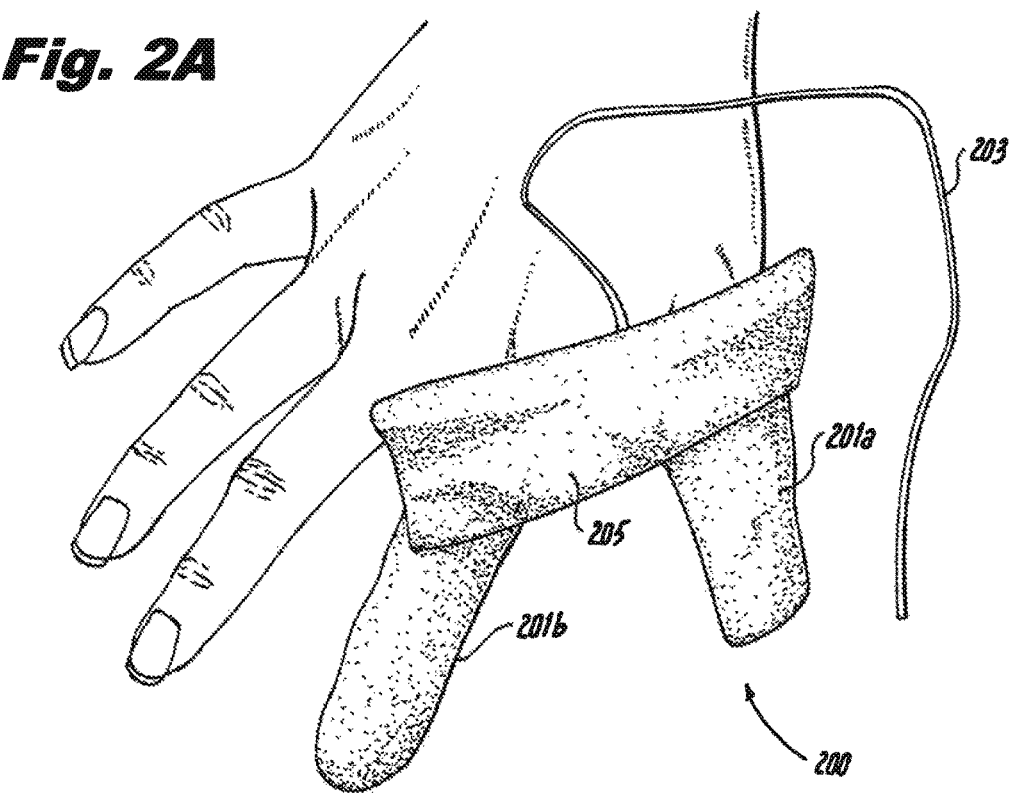
FIG. 2A is a perspective view of an embodiment of a dental finger glove device in accordance with this disclosure, shown disposed on a hand.
Figure 2B:
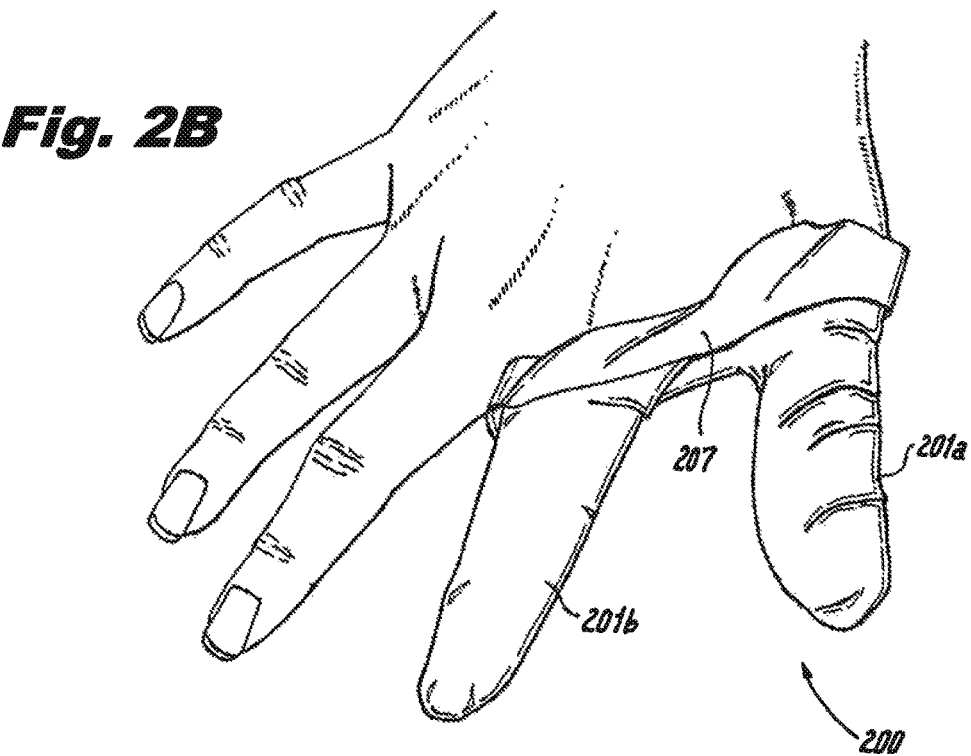
FIG. 2B is a top perspective view of the device of FIG. 2A, showing the mesh layer removed.
Figure 2C:
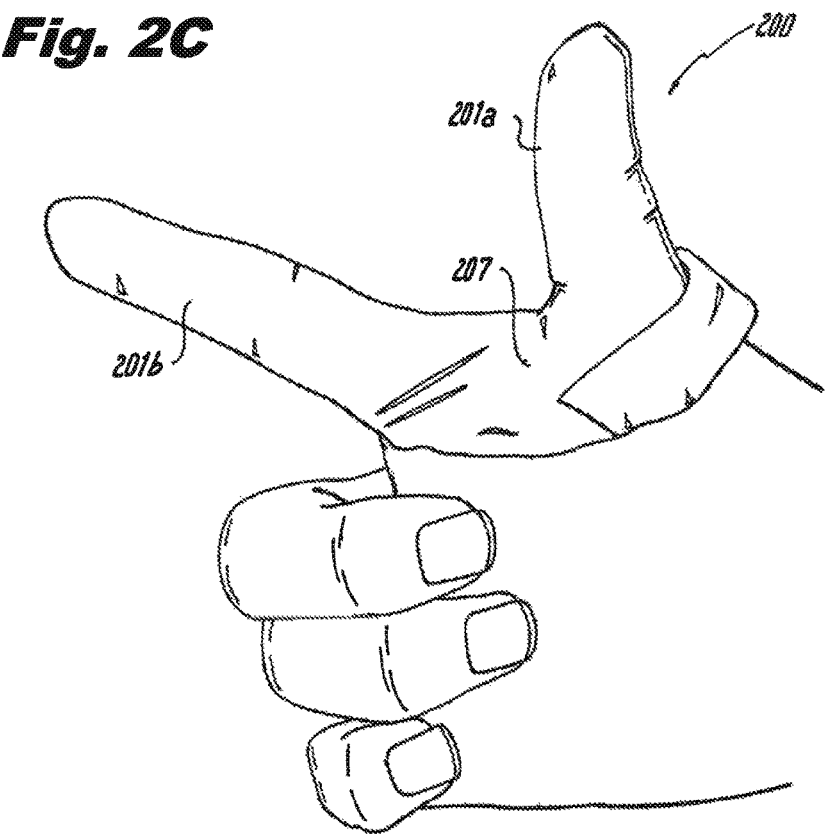
FIG. 2C is an underside perspective view of the device of FIG. 2A, showing the mesh layer removed.
Figure 2D:
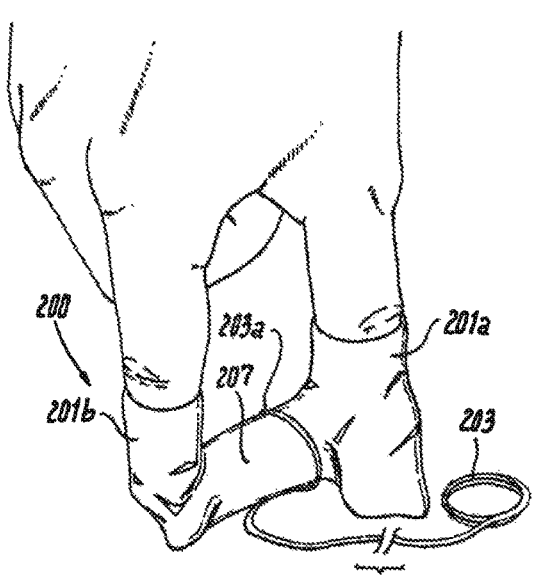
FIG. 2D is a perspective view of the device of FIG. 2A, showing the device pulled inside out and dental floss coiled up to be uncoiled and removed from the inside surface of the dental device.
Figure 2E:
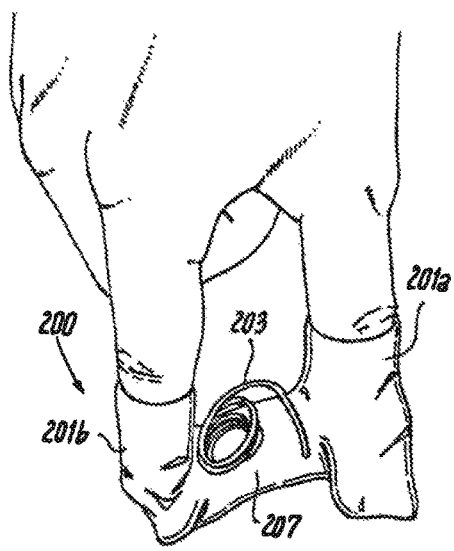
FIG. 2E is a perspective view of the device of FIG. 2A, showing the device pulled inside out and dental floss connected to an inner surface thereof and extended to be removed and/or used.

Referring to FIGS. 2D and 2E, dental floss 203 can be connected to an inner surface of the elastic two-finger glove 207. The dental floss 203 can be removably connected or permanently connected (e.g., bonding) to the elastic two-finger glove 207 in any suitable manner. In certain embodiments, the dental floss 203 can be perforated at a connection point to the elastic two-finger glove 207 such that it can be torn and removed therefrom. In this manner, when the user is finished scrubbing with the mesh material layer 205, the user can remove the device 300 while turning the device 200 inside out and then extend or remove the dental floss 203 from the device 200 for use in flossing.

It is contemplated that a securement member (not shown) can be attached to and extend from at least one of the first finger portion and the second finger portion for securing the device 200 to a user's hand. The securement member can be an elastic band for securing to the wrist of a user or any other suitable band.

Figure 3A:
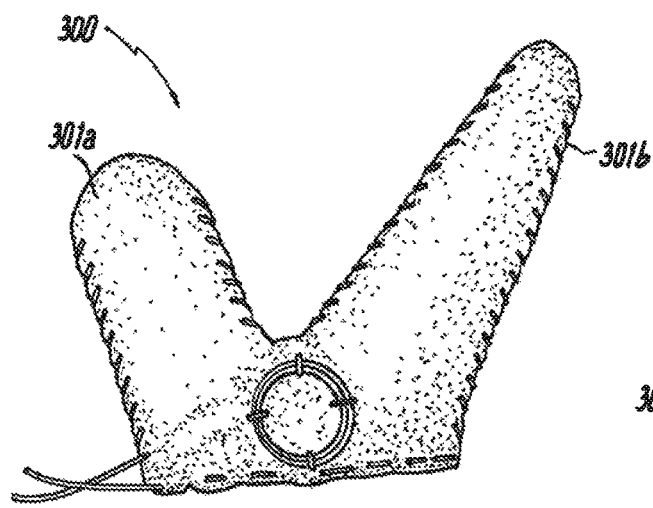
FIG. 3A is a side view of an embodiment of a dental finger glove device in accordance with this disclosure.
Figure 3B:
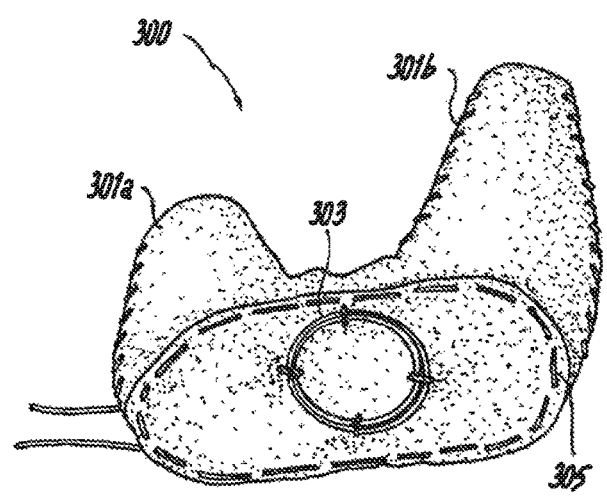
FIG. 3B is a rear perspective view of the device of FIG. 3A, showing the opening of the device and a dental floss coil disposed therein.
Figure 3C:
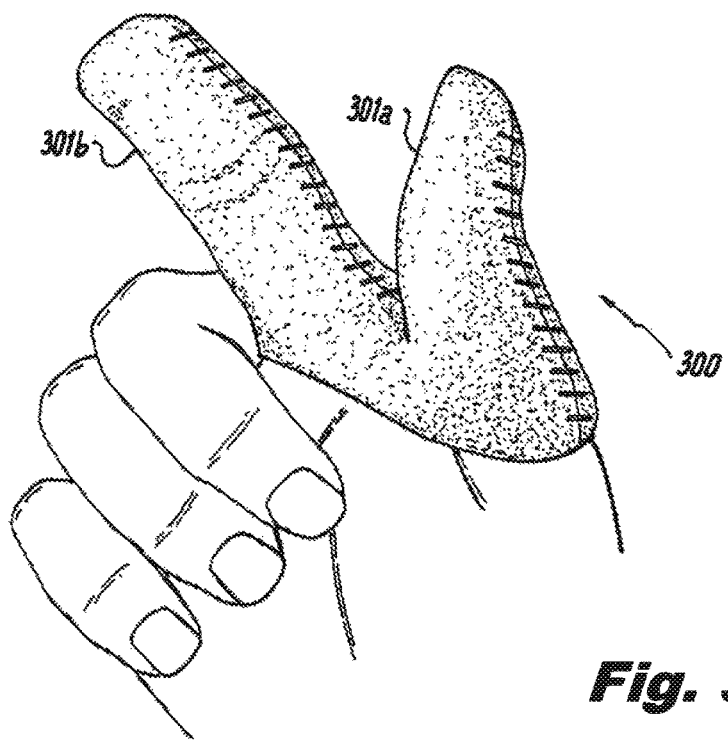
FIG. 3C is an underside perspective view of the device of FIG. 3A, shown disposed on a hand.

Referring to FIGS. 3A-3C, a dental finger glove device 300 can be made from only a mesh material without an elastic glove core. In this way, the device 300 can be less bulky, thinner, and lighter for packaging. The device 300 includes a first finger portion 301a and a second finger portion 303b similar to those described above.

It is contemplated that the device 300 can be made from a material that includes elastic fiber with pores and is mesh-like to retain a dental compound and to catch debris. The elastic fiber material can also be configured to act as a liquid barrier to prevent liquids (e.g., water, saliva, bodily fluids) from contacting the user's fingers. The elastic fiber material can be flexible to reach all areas of teeth, gums and tongue, and/or textured for mechanical debridement and massaging effect.

Dental floss 303 can be attached to the inside surface of the mesh material in any suitable manner as described above for removal and/or other use. In this manner, when the user is finished scrubbing with the mesh material, the user can remove the device 300 while turning the device 300 inside out and then extend or remove the dental floss 303 from the device 300 for use in flossing. As shown, the dental floss 303 can be attached in a coiled manner but removable by tearing the coil away from the mesh material.

The dental finger glove device 300 can include a securement portion 305 defining the opening to allow the user to insert their fingers into the device 300. As shown, the securement portion 305 can be adjusted to change the size of the opening and secure to a user's hand.

It is also contemplated that any of above described devices 100, 200, or 300 can be packaged dry or soaked in suitable liquids (e.g., ionized water and/or suitable dental compounds) to be ready for use upon removal from the package. In soaked embodiments, the mesh material can be wetted and packaged such that a user need not wet the device before use.

In accordance with at least one aspect of this disclosure, a method for manufacturing a dental device includes forming an elastic two-finger glove and disposing a mesh material on an outer surface of the elastic two finger glove. The method can further include coupling a dental floss to an inner surface of the elastic two-finger glove.

Coupling the dental floss to an inner surface of the elastic two-finger glove includes removably coupling the dental floss to the inner surface of the elastic two-finger glove. Removably coupling the dental floss to an inner surface of the elastic two-finger glove includes perforating a connection point of the dental floss.

The method can further include disposing a dental compound on or within the mesh material. In certain embodiments, the method can further include wetting the mesh material and packaging the dental device in a wetted state.

The herein disclosed devices can serve as supplement or replacement for tooth brushing, gum maintenance, and/or tongue brushing. For example, for babies, parents can opt to use herein disclosed devices to wipe gum tissue with a gentle massage to reduce milk, bad breath, and *Candida* infections. For toddlers, i.e., children under 3 years old, parents can use peroxide and transition to toothpaste. For 3-6 year olds, the mesh material can be impregnated with fluoride free toothpaste (e.g., MI Paste with Recaldent). For 6-12 year olds, the herein described devices can be packaged with fluoride toothpaste in moisturized sleeves with floss attached.

For adults any suitable dental compounds can be used depending on the desired effect. For example, devices as described herein can be packaged including dental compounds for everyday hygiene and cavity control, whitening and cavity control (e.g., using baking soda, hydrogen peroxide as whitening agents), gum disease treatment and cavity control (e.g., gum inflammation ingredients), and/or xerostomia control (e.g., baking soda, glycerin, lisosyme). The herein described devices can be configured for use with pets as well (e.g., cats, dogs).

It is also contemplated that at least some embodiments of herein disclosed devices can be configured for use with animals for animal dental care which would be made easier with the two finger design. The herein disclosed devices can also be configured for use as a denture cleansing device and/or impregnated with one or more denture care compounds for maintaining dentures and/or brushing gums of denture wearers.

Some benefits to the herein described devices include flexibility and the ability to use two fingers for massaging and squeezing the gums which can help with inflammation. Also, the mesh material can be porous enough to help remove food and other debris from between teeth. The herein described devices can be packaged and use for on-the-go dental care where the use of a toothbrush is difficult or impossible.

The devices, methods, and systems of the present disclosure, as described above and shown in the drawings, provide for dental finger gloves with enhanced properties over the art. While the apparatus and methods of the subject disclosure have been shown and described with reference to embodiments, those skilled in the art will readily appreciate that changes and/or modifications may be made thereto without departing from the spirit and scope of the subject disclosure.

What is claimed is:

1. A dental finger glove device, comprising:
a first finger portion configured to fit on a first digit of a user;
a second finger portion configured to fit on a second digit of a user and connected to the first finger portion;
wherein an outer surface of the finger portion includes a mesh material for massaging teeth, and
an elastic two-finger glove underneath the mesh material defining the first finger portion and the second finger portion, said glove configured to entirely cover only the first digit, the second digit and the thenar space and palmar and dorsal portions of the hand contiguous from the proximal end of the first digit to the proximal end of the second digit of a user and connecting the first and second digits of a user.

2. The device of claim 1, wherein the mesh is impregnated with a dental compound.

3. The device of claim 2, wherein the dental compound includes at least one of toothpaste, mouthwash, hydrogen peroxide, baking soda, Xylitol, Calcium Phosphate, Recaldent, Fluoride, Chlorhexidine, Propolis, an antioxidant, a neutralizing pH compound, an alkalizing pH compound, a foaming compound, a mechanical debridement compound, a chemical debridement compound, a biological debridement compound, vitamin E, vitamin A, vitamin C, vitamin K, Aloe Vera, chamomile or components thereof, mint or components thereof, peppermint or components thereof, cucumber extract or components thereof, carrot extract or components thereof.

4. The device of claim 2, wherein the mesh material is wetted and packaged such that a user need not wet the device before use.

5. The device of claim 1, wherein dental floss is connected to an inner surface of the elastic two-finger glove.

6. The device of claim 5, wherein the dental floss is perforated at a connection point to the elastic two-finger glove such that it can be removed therefrom.

7. The device of claim 1, wherein the mesh material includes gauze.

8. The device of claim 1, wherein the elastic two-finger glove includes at least one of rubber, latex, and/or other non-latex elastic.

9. The device of claim 1, further comprising a securement member attached to and extending from at least one of the first finger portion and the second finger portion for securing the device to a user's hand.

10. The device of claim 9, wherein the securement member is an elastic band for securing to the wrist of a user.

11. A dental finger glove device, comprising:
a first finger portion configured to fit on a first digit of a user;
a second finger portion configured to fit on a second digit of a user and connected to the first finger portion;

wherein an outer surface of the finger portion includes a mesh material for massaging teeth, and an elastic two-finger glove underneath the mesh material defining the first finger portion and the second finger portion, said glove configured to entirely cover only the first digit, the second digit and the thenar space and palmar and dorsal portions of the hand contiguous from the proximal end of each of the first digit to the proximal end of the second digit of a user and connecting the first and second digits of a user, wherein the part of the glove configured to cover a portion of the hand connecting the first and second digits of a user encloses the mesh material when turned inside out.

12. A method for manufacturing a dental device, comprising;

forming an elastic two-finger glove; and disposing a mesh material on an outer surface of the elastic two finger glove;

wherein, said glove is configured to entirely cover only the first digit, the second digit and the thenar space and palmar and dorsal portions of the hand contiguous from the proximal end of the first digit to the proximal end of the second digit of a user and connecting the first and second digits of a user.

13. The method of claim 12, further comprising coupling a dental floss to an inner surface of the elastic two-finger glove.

14. The method of claim 13, further wherein coupling the dental floss to an inner surface of the elastic two-finger glove includes removably coupling the dental floss to the inner surface of the elastic two-finger glove.

15. The method of claim 14, further wherein removably coupling the dental floss to an inner surface of the elastic two-finger glove includes perforating a connection point of the dental floss.

16. The method of claim 12, further comprising disposing a dental compound on or within the mesh material.

17. The method of claim 12, further comprising wetting the mesh material and packaging the dental device in a wetted state.

* * * * *